Figure 1:
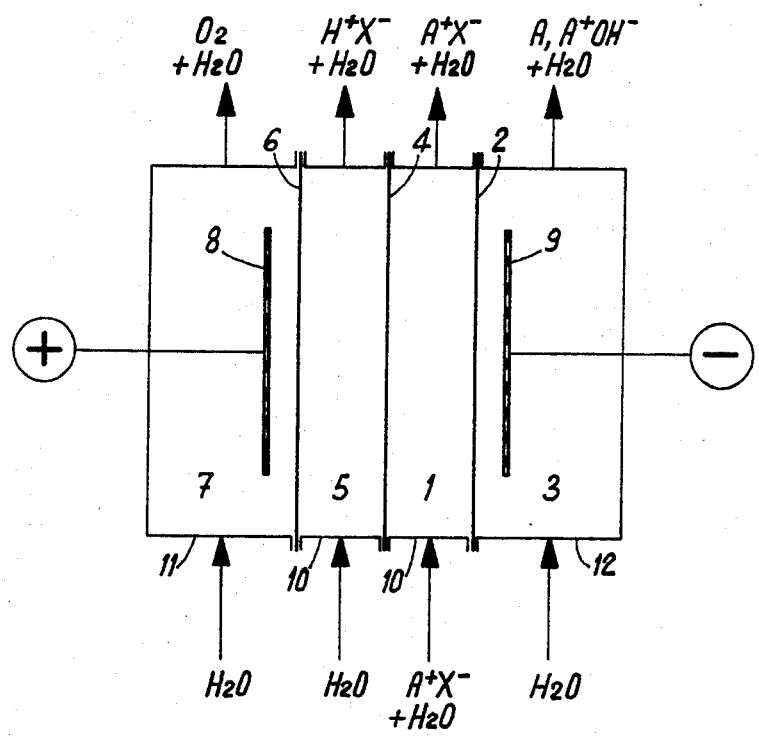

United States Patent [19]

De Witt et al.

[11] Patent Number: 4,521,285
[45] Date of Patent: Jun. 4, 1985

[54] ELECTROLYTIC PROCESS FOR THE PREPARATION OF ORGANIC COMPOUNDS

[76] Inventors: Paolo De Witt, via della Divisione Torino, 57 Rome; Enrico Benedetto, via P. Ferraris 31, Domodossola Novara, Italy

[21] Appl. No.: 551,817

[22] Filed: Nov. 15, 1983

[30] Foreign Application Priority Data

Nov. 25, 1982 [IT] Italy .................................. 24432 A/82

[51] Int. Cl.³ .......................... C25B 3/00; B01D 57/02
[52] U.S. Cl. .................................... 204/72; 204/182.4
[58] Field of Search ...................... 204/72, 180 P, 252, 204/253, 257, 299 R

[56] References Cited

U.S. PATENT DOCUMENTS

| | | | |
|---|---|---|---|
| 2,363,386 | 11/1944 | Bock | 204/72 |
| 2,737,486 | 3/1956 | Bodamer | 204/72 |
| 3,086,928 | 4/1963 | Schulz | 204/72 |
| 4,057,483 | 11/1977 | Giuffrida | 204/180 P |
| 4,425,202 | 1/1984 | Sullivan | 204/72 |

Primary Examiner—John F. Niebling
Attorney, Agent, or Firm—Pollock, Vande Sande & Priddy

[57] ABSTRACT

There is described an electrolytic cell and a process for removing the halide or other anion from an organic salt having as general formula $A^+X^-$, wherein $A^+$ is an organic cation and $X^-$ is a halide or other anion. Typical compounds of this type are the hydrohalides of nitrogen bases or other salts or hydrosalts of such bases or compounds notably salts (hydrohalides) of quaternary ammonium bases or of amines or amides. However the process herein contemplated may be applied to the removal of anions, e.g. chloride, which are present as an impurity or in combination with the organic compound.

16 Claims, 1 Drawing Figure

ELECTROLYTIC PROCESS FOR THE PREPARATION OF ORGANIC COMPOUNDS

The present invention relates to an electrolytic process for preparing organic compounds, and an electrolysis cell specifically intended for that process.

More specifically, the invention refers to an electrolytic cell and a process for removing the halide ion or other anion from an organic halide or other organic salt having the general formula $A^+X^-$, wherein $A^+$ is an organic cation and $X^-$ is a halide ion or other anion. In particular, the removal of the halide ion or of other anion may involve the conversion of the organic salt $A^+X^-$ into the corresponding free base, according to the scheme: $A^+X^- \rightarrow A^+OH^-$.

Alternatively, the organic cation $A^+$ may comprise both a basic functional group and an acid functional group; the removal of the halide or other anion involves then the conversion of the organic salt $A^+X^-$ into the corresponding inner salt, or electrically neutral compound, according to the scheme: $A^+X^- \rightarrow A$. Many such compounds are hydrohalides or halides of nitrogen bases like nitrogen compounds such as quaternary ammonium bases, organic amines, amides etc., while the invention is particularly concerned with halide or hydrohalide removal, it may also be applied for the removal of anions including hydroanions and other corresponding anions such as chloroacetates, chloropropionates, sulphonates, phosphates, borates, cyanides, thiocyanates, thiosulphates, isocyanates, sulphites, bisulphites, oxalates, etc.

In general, for example, the removal of halides ions from organic compounds which contain them is effected, according to the prior art, by making a solution of the organic halide flow through a column filled with a ion-exchange resin. The use of the ion-exchange resin columns, however, brings about several inconveniences. In fact, in order to recover with acceptable yields the de-halidized compound which flows out of the resin columns, it is necessary that these are abundantly washed, and this involves the production of a diluted solution of the de-halidized compound, solution that is to be re-concentrated before it undergoes the subsequent steps of the process. When resins are used, moreover, it is necessary to regenerate and wash the same, so that they can be re-utilized. The resin regeneration is carried out by means of alkaline solutions which, to be re-utilized, must also be purified and reconcentrated (see the Italian Patent Appln. No. 21015 A/82 filed on Apr. 30, 1982). Such resin regeneration process, washing of columns and reconcentration of the effluent solutions considerably affect the plant and operation costs and the elimination thereof would result in a clear advantage. Another inconvenience that the use of ion-exchange resin columns may present occurs when the de-halidized compound tends to quickly hydrolize, that is over a period of time that is inferior or equal to its permanence in the column.

It occurs, as a consequence, a partial hydrolytic degradation of the de-halidized compound, before one has the time to subject such compound to the subsequent working or reaction step. It is therefore an object of the present invention to provide a process and an electrolytic cell for that process which allow to remove the halide ions from organic halides which contain them, avoiding thus substantially all the inconveniences present in the known methods actually used for the same purposes, and particularly those inconveniences caused by the use of the ion-exchange resin columns.

The present invention avoids or minimizes the inconveniences of the prior art by providing a new process, whereby a relatively simple method and apparatus is used, to produce an acid, hydrogen and a solution containing either the corresponding free base of the organic cation or, alternatively, in the event that the particular organic cation comprises both a basic functional group and an acid functional group, a solution containing the corresponding inner salt, starting from a solution of the organic salt, water and electric energy.

The process of the invention comprises the steps of: conducting electrolysis of the compound to the subjected to anion removal in a cell comprising an anodic compartment, containing an anode, a cathodic compartment, containing a cathode, and two intermediate compartments: a pre-anodic compartment $C^1$ and a pre-cathodic compartment $C^2$, the anodic compartment being separated from the pre-anodic compartment $C^1$ by a cationic membrane $MC^1$, the cathodic compartment being separated from the pre-cathodic compartment $C^2$ by a cationic membrane $MC^2$, and the intermediate compartments $C^1$ and $C^2$ being separated by an anionic membrane MA.

The compound to be dehalogenated or otherwise treated to remove anions is fed into the pre-cathodic compartment $C^2$ generally as a solution or suspension in water or other polar solvent. The solution in the anodic compartment is generally an acid supporting solution. The cathodic compartment and the pre-anodic compartment $C^1$ are fed with water or other polar solvent so that, at the passage of electric current through the cell, hydrogen ions pass from the anodic to the $C^1$ compartment through the cationic membrane $MC^1$, halide ions or like anions, pass from the $C^2$ to the $C^1$ compartment through the anionic membrane MA, and the organic cations pass from the $C^2$ to the cathodic compartment through the cationic membrane $MC^2$.

At the anode the anions of the acid supporting solution oxidize, the hydrogen ion and the halide or like anion, by reaction, produce the corresponding acid in the pre-anodic compartment $C^1$, and water is reduced at the cathode producing hydrogen in the cathodic compartment. The acid solution is removed from the pre-anodic compartment $C^1$ and the hydrogen and the solution containing the organic cations in the form of a solution or suspension of the free base or inner salt of the organic is recovered from the cathode compartment.

The nature of the acid or acid supporting solution in the anodic compartment may vary, as this solution does not take direct part in the electrochemical process of, for example, the de-halidization of the organic halide. It is preferably an aqueous solution of an organic or inorganic hydroxy acid, e.g. sulphuric acid, phosphoric acid or acetic acid, or even an acid solution of a salt consisting of a hydroxy acid and any kind of cation, such as for instance iron sulphate, copper sulphate or sodium acetate. In general where halide is to be removed from the organic compound, the anode compartment should not contain halide in concentration high enough to evolve halogen (e.g. chlorine) at the anode.

At the anode the following phenomena can occur: discharge of oxygen from direct oxidation of the dilution water, or electrolytic oxidation of the hydroxy acid in the relevant peracid, or of the salt in the relevant persalt. For instance, by feeding the anodic compartment with sulphuric acid and employing an anode characterized by a low oxygen overvoltage (inferior or equal to about +2.0 V in normal hydrogen scale), e.g. titanium coated with a deposit of mixed oxides containing a noble metal oxide, at the anode there develops oxygen in the gaseous form, that can be recovered from the anodic compartment. Of course, to keep the right acid concentration, it is sufficient in this case to restore water in the anodic compartment by adding demineralized water.

When desired, it is possible, by using an anode having, in respect of the oxygen discharge, a sufficiently high overvoltage (greater than or equal to 2.1 V in normal hydrogen scale) to favour the electrolytic oxidation of the hydroxy acid in the relative peracid with respect to the oxygen discharge at the anode. For instance, with a lead or platinum anode and by means of a sulphuric acid solution, it is possible to oxidize the sulphuric acid in persulphuric, and to eliminate completely the evolution of elemental oxygen at the anode. In this case, the solution flowing out of the anodic compartment, which contains sulphuric and persulphuric acid, can be reacted in an external reactor with water, whereby it will give hydrogen peroxide, according to the known reaction:

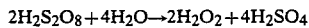

$$2H_2S_2O_8 + 4H_2O \rightarrow 2H_2O_2 + 4H_2SO_4$$

and the anodic compartment of the cell can therefore be fed again with sulphuric acid. It is also possible, on the other hand, to exploit the anodic reaction to oxidize a salt into the relative persalt. For example, by charging the anodic compartment with ferrous sulphate, the same can be oxidized into ferric sulphate, and the solution containing ferric sulphate effluent from the anodic compartment can be recovered; in this case two it is possible to completely eliminate the development of oxygen at the anode. Likewise, it is possible to add to the water with which the cathodic compartment has been fed, both in solution and in suspension, compounds which, although they do not interfere with the water reduction at the cathode, serve for complexing or salifying with the organic cations, so as to favour the subsequent working steps.

With reference to FIG. 1, which schematically illustrates the configuration of the electrolytic cell and the manner by which the process herein contemplated is performed, the cell consists of a separation pre-cathodic compartment 1, there being present, on the cathodic side, a membrane 2 of cation-exchange resin or other material, permeable to and able of transferring cations but generally not substantially permeable to electrolyte flow therethrough (cationic membrane), said membrane separating said pre-cathodic compartment 1 from the cathodic compartment 3, as well as a membrane 4 of anion-exchange resin or other material, permeable to and capable of transferring anions (anionic membrane), which separates the pre-cathodic compartment 1 from the pre-anodic compartment 5, wherein the halide or the like anion combines again to produce the relevant acid. The pre-anodic compartment 5, in its turn, is kept separated from the anodic compartment 7 by a membrane 6 of cation-exchange resin permeable to cations (cationic membrane).

As a general rule all of these membranes are impermeable or substantially impermeable to flow of electrolyte from one side thereof to the other.

In FIG. 1 there are also indicated the feeding and recovering points of the reagents and the products.

In the anodic compartment there is an anode 8, preferably of metal such as e.g. titanium, tantalum, zirconium, hafnium or alloys of the same, the surface thereof being at least partly coated with a non passivable and catalytic film for the development of oxygen from aqueous acid solutions or for the oxidation of the hydroxy acid or salt into the relative peracid or persalt. Graphite, lead and similar anodic consumable materials may also be used, but, being subject to anodic dissolution, they may give rise to contamination of the cationic membrane, besides not being permanent. The more permanent and/or insoluble anodes generally have a non passivable catalytic film which may comprise metallic noble metal such as platinum, iridium, rhodium or alloys thereof, or a mixture of electroconductive oxides, comprising at least one oxide or mixed oxide of a noble metal, such as platinum, iridium, ruthenium, palladium and rhodium. In case it is preferredly sought to favour the oxygen development at the anode with respect to the oxidation of the acid into peracid, it is particularly suitable a coating of mixed oxides, comprising at least one valve metal oxide such as an oxide of titanium, tantalum or zirconium, and at least one noble metal oxide such as an oxide of ruthenium and iridium, obtained by thermal decomposition of metal salts. Such film, in fact, is characterized by a low overvoltage to the development of oxygen.

In the cathodic compartment there is located a cathode 9 of a material resistant to catholyte, and preferably provided with a surface having a low overvoltage to the hydrogen discharge from aqueous solutions. Suitable materials for the cathode are monel, hastelloys, nickel, stainless steel, copper and silver. To the purpose of reducing the overvoltage, the cathode may be coated with a layer of material catalytic to the hydrogen discharge, such as e.g. the noble metals such as platinum, ruthenium, iridium, palladium, rhodium, alloys thereof, oxides thereof and Raney nickel. Both the anode and the cathode can be made of solid plate, and properly serve as bottom walls of the respective anodic and cathodic compartments. It is however more advisable to make both the anode and the cathode foraminous for example of screen or expanded metal, welded on suitable current leads, to reduce the so-called bubble effect, that is the screening action of the gas bubbles which form on the surface of the electrodes, and to which a remarkable ohmic drop is attributable. The screen or expanded metal electrodes, besides increasing the actual surface and reducing therefore the kinetics at the electrodes, for the same currend load, allow a better disengagement of the gas bubbles and, consequently, a reduction of the resistive voltage losses during working.

In addition, the foraminous electrodes are most advantageously employed to bear directly against the surface the two cationic membranes which delimit the anodic and cathodic compartments. The membranes used to divide the electrolytic cell in the respective compartments and to selectively diffuse the ions are preferably mounted in the cell on supporting nets (not shown in the figure) of inert materials, such as e.g. polytetrafluoroethylene, ethylene and propylene fluorinated copolymers, polypropylene, asbestos, titanium, tantalum, niobium or noble metals. As an alternative the use of supporting nets or grids, a resilient pad, easily permeable to the flow of electrolytes, consisting of one or more superimposed layers of cloth made of fine threads of the same material cited above may be placed in both the intermediate compartments 1 and 5. The two resiliently compressable pads are compressed during the closing of the cell and, thanks to their elasticity, they provide a certain elastic reaction force which tends to space apart the membranes, thus providing the contact between the membranes and the anode 8 and cathode 9, against which respectively the membrane 6 and the membrane 2 are forced by the elastic pressure exerted by the two resilient pads.

The anionic and cationic membranes used belong to the well known classes of organic commerical polymers, originally often of thermoplastic type, containing polar groups of anionic and cationic kind in the form of thin films.

The membranes are capable of transferring either anion or cation, i.e. they are permeable to certain kinds of ions but substantially less permeable or even impermeable to others. Certain ions, apparently through a ionic exchange process with the polar groups of the polymer, are capable of passing through the membrane, whilst other ions, of opposite charge, are not capable of doing that.

The preparation and structure of anionic and cationic membranes are exhaustively described in the chapter entitled "Membranes" (Encyclopedia of Polymer Science and Technology, published by H. Wiley and Sons, New York, 1968, vol. 8, pages 620-638) of which express reference is made herein to the pertaining matter. In addition to the above, the following commerical membranes may be regarded as specimens of preferred membranes in the embodiment of the present invention:

Anionic membranes:
AMFLON series 310, based on fluorinated polymer substituted with quaternary ammonium, produced by the firm American Machine and Foundary Co., U.S.A.
Ionac MA 3148, MA 3236 and MA 3475, based on polymer substituted with quaternary ammonium derived from heterogeneous polyvinyl chloride, produced by the firm Ritter-Pfaulder Corp., Permutit Division, U.S.A.

Cationic membranes:
Ionac MC 3142, MC 3235 and MC 3470XL, based on polymer substituted with polysulphates derived from heterogeneous polysulphates derived from heterogeneous polyvinyl chloride, produced by the firm Ritter-Pfaulder Corp., Permutit Division, U.S.A.;
Nafion XR type, hydrolized copolymer of fluorinated olefin and of a perchloro fluorosulphonate vinyl ether, produced by the firm E.I. Du Pont de Nemours and Co. Inc., U.S.A.

The closing frames 10 of the intermediate compartments, as well as the two head units (anodic 11 and cathodic 12) are made of conventional materials, such as e.g. steel or another mechanically resistant material, internally coated with mastic or synthetic rubbers, such as neoprene, polyvinylidene chloride, polyesters, polypropylene, polyvinyl chloride, polytetrafluoroethylene or other suitable plastics. Closing frames and head units of different rigid materials, such as e.g. rigid polyvinyl chloride, polyvinylidene chloride, polypropylene or phenol-formaldehyde resins may be used, instead of coated steel, preferaly if reinforced with fibers. The seals are of traditional materials such as natural and synthetic rubbers.

The cell compartments are usually separated the one from the other by flat membranes; other shapes, however, besides the parallelepiped, can be used, such as cylindrical or saw toothed or fingered shapes.

According to a preferred embodiment of the present invention, for treating an organic halide, before starting the electrolysis process in the cell illustrated in FIG. 1, there is provided the step of filling the anodic compartment 7 with an aqueous solution of an hydroxy acid, preferably sulphuric acid, at a concentration ranging from 0.05 N to 4 N, more preferably comprised between 0.3 and 2 N, then the pre-anodic compartment 5 is filled with demineralized water or with a diluted solution or hydracid; an aqueous solution of the organic halide of the general formula $A^+X^-$ is circulated in the pre-cathodic compartment 1, and water, or an aqueous acid solution or suspension is circulated in the cathodic compartment 3.

The suitable polarization of the cell, that is the application to the electrodes of a difference of potentials capable of causing the passage of an electric current through said cell involves the migration of the halide ion $X^-$ through the anionic membrane 4 into the pre-anodic compartment 5, and, at the same time, the migration of the organic cation $A^+$ through the cationic membrane 2 into the cathodic compartment 3. The halide ion, on the other hand, is prevented from reaching the anode because of the presence of the cationic membrane 6. Therefore, the passage of current brings about the discharge of oxygen at the anode, and the contemporary migration of $H^+$ ions through the cationic membrane 6 in the pre-anodic compartment 5, wherein the corresponding hydracid is generated. The hydracid concentration in the pre-anodic compartment 5 generally is kept constant by dilution with water, and discharging the acid solution at the pre-determined concentration.

Likewise, the anolyte concentration is kept at the pe-established value by restoring the dissociated water and the hydration water carried by the $H^+$ ion through the cationic membrane 6. It was found that, in order to avoid polarization phenomena caused by concentration gradients on the opposite surfaces of the cationic membrane 6, it is preferable to keep the anolyte and hydracid concentrations in the pre-anodic compartment 5 such that the equivalent normality of the two solutions is almost the same. Therefore, also the hydracid concentration in the pre-anodic compartment 5 is preferably kept to normalities comprised between 0.3 and 2 N. This can be easily obtained by properly adjusting the feeding of dilution water in the anodic and pre-anodic compartments.

The impoverished solution of organic halide, flowing out of compartment 1, may be properly re-concentrated and re-circulated in the cell.

To the water of the solution, or the acid suspension put in the cathodic compartment there can be added acid compounds capable of reacting with or promoting salification of the organic cation migrating into the cationic compartment. Such acid compound may be both in solution and/or in suspension Typical such compounds include camphoric, di-benzoyl-tartaric, N-acetyl-glutamic acid.

The electrolysis is carried out by maintaining an electric potential between anode and cathode high enough to cause the desired electrolysis and the cell temperature is kept higher than the freezing temperature of the solutions contained in the cell, that is at about 20° C., and generally lower than the temperature at which the degradation of the de-halidized compound could occur, for example below about 70° C.

The current density is normally maintained between 500 A/m² and 3000 A/m², although other current densities may be resorted to, and is usually optimized according to the specific cases, through a series of tests. This is done with a view to obtaining the best compromise between the heat balance requirements and the necessity or desirability of keeping the cell voltage low, in order to maintain an high overall energy efficiency of the electrolytic process.

The total inter-electrode distance may be as high as about 1 or more centimeters. As a rule, if the width of the intermediate compartments is kept at about 5 millimeters, the distance between the electrodes may be advantageously kept below 15-20 millimeters. The distance between the electrodes and the current desnity being as indicated above, the cell tension may range between 5 and 10 volts at relatively low current densities, and between 10 and 25 volts at higher current densities. Usually, the electrolysis is effected at atmospheric pressure, although it may also be effected at a lower or higher pressure. The electrolytic cell and the process of the present invention are of general applicability, that is to say they can be advantageously applied in all those organic syntheses in the course of which the removal of halide or like anions from intermediates or halongenated starting products was (or would be) generally carried out by using ion-exchange resins. Thus organic salts of the general formula A⁺X⁻ which are dissociated in polar solvent such as water may be treated according to the process of the invention to remove the anion X⁻ and for recovering the organic cation as a free base A⁺OH⁻ or as its corresponding inner salt A°. Some examples of compounds of this type are:

Monoalkyl trimethyl Quaternaries

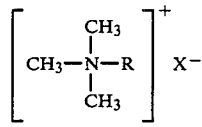

X = chloride or methyl sulphate
R = (a) aliphatic, saturated or unsaturated, C₁₂-C₂₂ chain lengths
    (b) allyl-
    (c) benzyl- Monomethyl Trialkyl Quaternaries

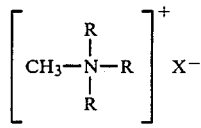

X = chloride
R = aliphatic alkyl, normal or branched, C₈-C₁₈

Imidazolinium Quaternaries

-continued

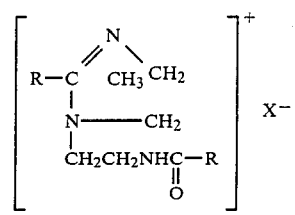

X = methyl sulphate CH₃SO₄⁻
R = aliphatic, normal or unsaturated, C₁₂-C₁₈

Dimethyl Alkyl Benzyl Quaternaries

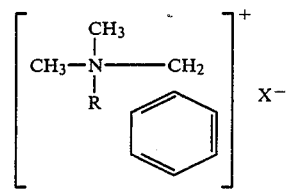

X = chloride
R = aliphatic, normal, C₁₂-C₁₈

Complex Diquaternaries

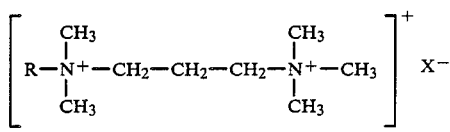

X = chloride
R = aliphatic, saturated or unsaturated

Dialkyl Dimethyl Quaternaries

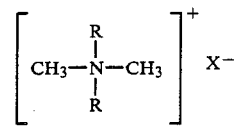

X = chloride or methylsulphate
R = aliphatic, saturated or unsaturated, normal or branched, C₈-C₂₂

Diamidoamine Based Quaternaries

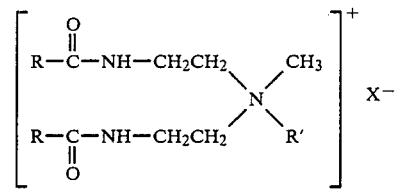

X = methyl sulphate
R = aliphatic, normal or unsaturated, C₁₂-C₁₈
R¹ = 2-hydroxyethyl
     2-hydroxypropyl Dialkyl Methyl Benzyl Quaternaries -continued

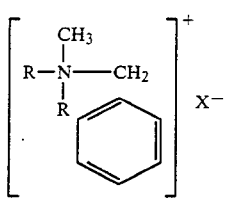

X = chloride
R = hydrogenated tallow

Quaternary ammonium compound represented by the general formula

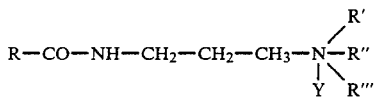

where R is a member of the group consisting of aliphatic and alicyclic radicals containing at least 7 carbon atoms; R' and R'' are members of the group consisting of alkyl radicals having from 1 to 3 carbon atoms, inclusive, and monohydroxyalkyl radicals having from 2 to 8 carbon atoms, inclusive; R''' is a monohydroxyalkyl radical having from 2 to 3 carbon atoms, inclusive, and Y is the anion of an acid.

Representative examples of the anion Y are halide ions (that is Y can represent halogen, more particularly chlorine, bromine, fluorine or iodine), sulphate, sulphonate, phosphate, borate, cyanide, carbonate, hydrocarbonate, thiocyanate, thiosulphate, isocyanate, sulphite, bisulphite, nitrate, nitrite, oxalate, slicate, sulphide, cyanate, acetate and other common inorganic anions.

The organic salt may include an aliphatic chain of at least 8 carbon atoms which is linked to an anionic and/or cationic functional group. The cationic functional group may be represented by primary amino ($-NH_2$), secondary amino ($>NH$), tertiary amino ($\diagdown \!\!\!-\!\! N \!\!\!-\!\!\! \diagup$), quaternary ammonium ($\diagdown \!\!\!-\!\! N^+ \!\!-\!\!\! \diagup$), hydrazino ($-NH-NH_2$), azonium ($-NH-NH^+ \!\!-\!\! \diagup_{\diagdown}$), guanyl ($-C \underset{NH_2}{\overset{NH}{\diagup\!\!\diagdown}}$), guanido ($-NH-C\underset{NH_2}{\overset{NH}{\diagup\!\!\diagdown}}$)

biguanido ($-NH-\underset{NH}{\overset{}{\underset{\|}{C}}}-NH-\underset{NH}{\overset{}{\underset{\|}{C}}}-NH_2$) amine oxide ($\diagdown \!\!\!-\!\! N^{\!-}\!\!\!-\!\!\! \diagup \! O$)

ternary sulphonium ($\diagdown \!\!\!-\!\! S^+ \!\!-\!\!\! \diagup$) or quaternary phosphonium ($\diagdown \!\!\!-\!\! P^+ \!\!-\!\!\! \diagup$)

substituents.

The organic cationic portion A+ of the salt A+X− may also include both cationic functional groups and anionic functional group thus they may be represented as follows:

$(F^+-Q-A_nH)X^-$ or $(F^+-Q-A_nM)X^-$ wherein F+ represents an onium grouping, $A_n$ represents an acidic substituent of the type above, Q represents a bivalent organic grouping containing an aliphatic chain of at least 8 carbon atoms, M represents ammonium or an alkali metal, H is hydrogen and X− represents an anion such as for example an halide. These amphoteric substances, sometimes referred to as anpholytes, contain both cationic and anionic substitutents and they may form their inner salt upon removal of the anion X−. In particular it has been found that particularly advantageous results are obtained in the production of L(−) carnitine. The invention will now be illustrated by referring to a specific embodiment of the process of the invention as applied for the industrial preparation of L(−) carnitine, of which there are known various therapeutical applications.

It is known that L(−) carnitine is generally prepared by converting first an aqueous solution of D,L-carnitinamide chloride into D,L-carnitinamide base. This de-halidization of D,L-carnitinamide chloride is necessary in view of its subsequent salification with D-camphoric acid to the purpose of obtaining a solution containing the mixture of D-camphorate of the D-carnitinamide, and of D-camphorate of the L-carnitinamide. From the latter the D-camphorate of the L-carnitinamide is insulated by precipitating it by fractioned crystallization with a lower alkanol (1–5 carbon atoms), and separating it by filtration from the D-camphorate of D-carnitinamide, which remains in the solution. The D-camphorate of L-carnitinamide is then suspended in alkanol, and gaseous hydrochloric acid is bubbled in the suspension, obtaining as a result L-carnitinamide chloride. From the latter there is obtained by acid hydrolysis L(−) carnitine, which may be converted into L(−) carnitine inner salt.

Alternative processes for producing L(−) carnitine are based on the reaction between D,L-carnitinenitrile and D-camphoric acid, or between D,L-carnitinenitrile and L-acetylglutamic acid. In these processes too, howevwer, the first step is the conversion of a halide (in this case D,L-carnitinenitrile chloride) in the corresponding free base (D,L-carnictine, conversion that is necessary to allow the subsequent salification reaction with D-camphoric acid or L-acetylglutamic acid, respectively.

The following non-limiting examples are for illustrating the process according to the present invention. The cell used for the tests described by the examples had the configuration illustrated in FIG. 1, with an electrodic surface of 0.3 square meter. The anode 8 consisted of flattened sheet of 1.5 millimeters thickness, made of titanium, coated with a deposit of about 20 grams per square meter, consisting essentially of iridium (60%) and tantalum (40%) mixed oxide, obtained by thermal decomposition in furnace of a mixture of decomposable metal salts, produced by the firm Permelec SpA of Milan, under the commercial trademark of DSA(R) (dimensionally stable anode). The cathode 9 consisted of a flattened sheet of 1.5 millimeters thickness, of stainless steel AISI 316. The two cationic membranes 2 and 6 were both of Nafion(R) 324, produced by the firm E. I. Du Pont De Nemours & Co. U.S.A. The anionic membrane 4 was of the Ionac MA 3475 type, produced by the firm Ritter-Pfaulder Corp., Permutit Division, U.S.A.

The frames and the two head units of the cell were made of rigid polyvinyl chloride.

EXAMPLE 1

The compartment 1 of the electrolytic cell schematicaly illustrated in the drawing was filled with a solution containing 90 kilograms of D,L-carnitinamide chloride (DL (3carboxyamide-2-hydroxypropyl) trimethylammonium chloride) dissolved in 450 liters (about 20%) demineralized water. In the cathodic compartment 3 was circulated a suspension containing 90 kilograms of D-camphoric acid suspended in 100 liters demineralized water. 0.7 N sulphuric acid was introduced in the anodic compartment 7 and a solution of 0.5 N hydrochloric acid was introduced in the pre-anodic compartment 5. Demineralized water was then added in both the anodic and the pre-anodic compartments, to keep said concentrations constant during the cell working. The working conditions of the cell were as follows:
  temperature 50° C.
  current density 1000 A/m$^2$
  tension at the electrodes 15 to 22 V
  pH of the catholyte 5 to 6

The DL carnitinamide quaternary ammonium ion (DL (3 carboxyamide-2-hydroxypropyl) trimethylammonium) passed through the cation exchange membrane largely if not entirely by cation exchange, in the cathodic compartment, and salified with the D-camphoric acid giving as final result in about 30% solution of D,L-carnitinamide D-camphorate (around 500 liters). The cathode developed hydrogen was liberated in the atmosphere as well as the anode developed oxygen. Hydrochloric acid was recovered from the compartment 5 of the cell through a discharge in dilution water was being added in the compartment. The D,L-carnitineamide D-camphorate solution was dried. The residue was taken up with about 900 isobutyl alcohol, heating to 60° C. After the whole mass was diluted, it was cooled to 30° C. The crystallized product was filtered. 80 kg L-carnitinamide D-camphorate were obtained, with $[\alpha]_D^{20}$ comprised between +7 and +8. The product thus obtained was dissolved in 160 lt demineralized water, then was acidified at pH 3.5 with concentrated hydrochloric acid (37%). The precipitated D-camphoric acid was filtered and the solution was dry concentrated. To the residue, 26 lt of 37% by weight hydrochloric acid were added. The whole was heated for 7 hours at 70° C., then was cooled to 5° C., and the precipitated ammonium chloride was filtered. The solution containing L-carnitine chloride was treated as in Example 5.

EXAMPLE 2

The compartment 1 of the electrolytic cell was filled with a solution containing 90 kg of D,L carnitinenitrile chloride (DL (3 cyano-2hydroxypropyl) trimethylammonium chloride) dissolved in 450 lt demineralized water (20%). A suspension containing 90 kg N-acetyl-L-glutamic acid in 100 lt demineralized water was circulated in the cathodic compartment 3. The other working conditions were identical to those reported in Example 1, except for the tension at the electrodes, which was of 14 to 18 V. The DL carnitinenitrile quaternary ammonium ion (DL 3 cyano-2hydroxypropyl)-trimethylammonium) passed in the cathodic compartment, salified with the N-acetyl-L-glutamic acid giving as a final result a 30% solution of D,L-carnitinenitrile -N-acetyl-L-glutamate. The 30% solution of D,L-carnitinenitrile -N-acetyl-L-glutamate was dried (about 600 lt). The residue was taken up with 300 lt methyl alcohol, and heated to 60° C. until total dissolution, then was cooled to 0–5° C. About 75 kg of D-carnitinenitrile N-acetyl-L-glutamate crystallized, and were filtered.

The filtered solution was acidified with gaseous hydrochloric acid until pH 2. Then was brought to 20° C. and the precipitated product was filtered. 25 kg of L-carnititnenitrile chloride with $[\alpha]_D$ of $-24.5$ were obtained. This product could be hydrolized with concentrated hydrochloric acid, to obtain L-carnitine chloride, which could be converted in inner salt as described in Example 5.

EXAMPLE 3

The compartment 1 of the electrolytic cell was filled with a solution containing 90 kg of D,L-carnitinenitrile chloride (DL (3 cyano-2 hydroxypropyl) trimethylamino chloride) dissolved in 450 lt demineralized water (20%). In the cathodic compartment 3 was circulated a suspension containing 50 kg of D-camphoric acid (50% of the theoretical) in 100 lt demineralized water. The other working conditions of the cell were identical to those described in the example, except for the pH value of the catholyte. The D L-carnitinenitrile quaternary ammonium ion (DL 3 cyano-2hydroxypropyl) trimethylammonium) passed in the cathodic compartment, salified with the D-camphoric acid giving as a final result a 32% solution of D,L-carnitinenitrile D-camphorate with pH 11.2, because the dosage of the D-camphoric acid was kept on purpose at 50% of the stoichiometric. The solution (about 600 lt) effluent from the cell was treated with 87 lt of hydrogen per oxide at 40% P/V (130 vol.) and was allowed to react for 1 hour 50 kg D-camphoric acid were then added. The solution was clarified by filtration, and dried. Then was taken up with about 900 lt isobutyl alcohol, by heating to 60° C. After the mass had completely dissolved, was cooled to 30° C., and the precipitate was filtered. About 80 kg L-carnitinamide D-camphorate having a $[\alpha]_D$ comprised between +7 and +8 were obtained. Then the suitable steps were taken for the obtainment of L-carnitine inner salt, as described by the examples 1 and 5.

EXAMPLE 4

A solution containing 66 kg of L-carnitinamide chloride (L (3 carboxyamide-2-hydroxypropyl) trimethylammonium chloride) was circulated in the compartment 1 of the previously described electrolitic cell, in 200 lt demineralized water. Demineralized water was circulated in the cathodic compartment 3. The other working conditions of the cell were the same as those described in Example 1, except for the pH of the catholyte which, in this case, was about 12.5. In the cathodic compartment passed the L-carnitinamide quaternary ammonium ion (L (3-carboxyamide 2 hydroxypropyl)-trimethylammonium), the chloride ion passed into the compartment 5, forming hydrochloric acid. Oxygen developed at the anode, and the hydrogen ion discharged at the cathode, developing molecular hydrogen. The solution in the cathodic compartment was heated to a temperature comprised between 40° C. and 60° C., and kept circulating for about 40 hours at the pH conditions above indicated. In these conditions, all the L-carnitinamide base was converted in L-carnitine inner salt. The solution containing this product was vacuum concentrated at 60° C. until water was eliminated for the most part, then, by addition of isobutyl alcohol, a white crystalline product was obtained, which was filtered, washed with isobutyl alcohol and vacuum dried in atmosphere of de-humidified $N_3$ (a rather deliquescent product). 44 kg of product were obtained (yield 80%), in accordance with the characteristics of the L-carnitine inner salt.

EXAMPLE 5

The compartment 1 of the previously described electrolytic cell was filled with a solution containing 84 kg L-carnitine chloride (L (3-carboxy 2-hydrodypropyl) trimethylammonium chloride) dissolved in 180 lt demineralized water. The cathodic compartment was fed with demineralized water. The other working conditions of the cell were identical to those described in Example 1, except for the pH of the catholyte, which remained comprised between 6.5 and 7.5, without addition to the catholyte itself of acid solutions. In the cathodic compartment passed the quaternary ammonium ion (L-carnitine), whilst in the compartment 5 passed the chlorine ion, forming hydrochloric acid. Oxygen developed at the anode, while the hydrogen ion discharged at the cathode with developement of molecular hydrogen. From the cathodic compartment there was obtained a concentrated solution (about 30%) of L-carnitine inner salt, which was further concentrated under vacuum at 60° C. The L-carnitine inner salt was then precipitated and crystallized from isobutyl alcohol, as already described in Example 4. 62.7 kg (yield 89%) of white microcrystalline product were obtained, in accordance with the characteristics of the L-carnitine inner salt.

We claim:

1. A method for removing an anion from an organic compound comprising at least a cationic functional group and containing an anion as an impurity or in combination therewith and dissociable therefrom in a polar solvent which comprises conducting said removal in an electrolytic cell divided into a pre-cathodic compartment wherein a solution of the organic compound to be treated is disposed and which is separated from the cathodic compartment which contains a cathode, by a cation-exchange membrane a pre-anodic compartment separated from the anodic compartment, which contains an anode, by a cation-exchange membrane and the pre-anodic compartment separated from the pre-cathodic compartment by a anion-exchange membrane; disposing an acid electrolyte in the anodic compartment and water in the pre-anodic compartment and in the cathode compartment, passing an electrolysis current through the cell causing the anion to migrate from the pre-cathodic compartment through the anion-exchange membrane into the pre-anodic compartment to combine with the hydrogen ion migrating from the anode compartment through the cation-exchange membrane into the pre-anodic comparment to form the corresponding acid, and causing the organic cation to migrate from the pre-cathodic compartment through the cationexchange membrane into the cathodic compartment, wherein a solution containing the organic cation is obtained.

2. The method of claim 1 wherein the organic compound contains a cationic functional group and combines with an hydroxyl ion to form its free base in the cathodic solution.

3. The method of claim 1 wherein the organic compound contains both a cationic functional group and an anionic functional group and forms its inner salt in the cathodic solution.

4. The method of claim 1 wherein the anion is chlorine and hydrochloric acid is formed in the pre-anodic compartment and dilution water is let into the pre-anodic compartment.

5. The method of claim 4 wherein the acid in the anodic compartment is of a different anion than an halide ion.

6. The method of claim 1 wherein the acid electrolyte in the anodic compartment is an aqueous solution of sulfuric acid, oxygen develops at the anode and dilution water is let into the anodic compartment.

7. The method of dehalogenating an organic amine hydrohalide which comprises conducting an electrolysis in a cell having a pair of opposed electrodes respectively disposed in an anodic compartment and in a cathodic compartment which compartments are separated from two central compartments, a pre-anodic compartment and a pre-cathodic compartment by cation-exchange membranes and the two central compartments are separated by an anion-exchange membrane, passing the organic amine hydrohalide through the pre-cathodic compartment and maintaining an electrolytic potential between the electrodes to cause migration of halide ion through the anion-exchange membrane to the pre-anodic compartment and the organic amine ion through through the cation-exchange membrane to the cathodic compartment.

8. The method of claim 7 wherein hydrogen haide is collected and withdrawn from the pre-anodic compartment.

9. The method of forming a quaternary ammonium salt which comprises causing a quaternary ammonium organic ion to migrate through a cation exchange membrane inserted in a multi-compartment electrolytic cell from one side to the other side of said membrane, maintaining a reactive organic acid on said other side of the membrane and reacting said organic acid with said quaternary ammonium organic ion.

10. The method of claim 9 wherein said migration is effected by maintaining an electric potential on opposite sides of said membrane to cause the quaternary ammonium organic ion to migrate toward the cathode.

11. A method according to claim 2 for producing L(−) carnitine, wherein said organic compound is selected from the grup of D,L-carnitinamide halide and D,L-carnitinenitride halide.

12. A method according to claim 4 for producing L(−) carnitine inner salt, wherein said organic compound is selected from the group of L-carnitinamide halide and L-carnitine halide.

13. A method according to claim 1 wherein the concentration of said acid electrolyte in said anodic compartment is 0.05N to 4N.

14. A method according to claim 1 wherein the concentration of said acid electrolyte in said anodic compartment is 0.3N to 2N.

15. A method according to claim 1 wherein the temperature is about 20° C. to below about 70° C.

16. A method according to claim 1 wherein the current density is 500 $A/m^2$ to 3000 $A/m^2$.

* * * * *